(12) United States Patent
Mutz

(10) Patent No.: US 7,879,860 B2
(45) Date of Patent: Feb. 1, 2011

(54) DELTA AND EPSILON CRYSTAL FORMS OF IMATINIB MESYLATE

(75) Inventor: Michael Mutz, Freiburg (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/064,637

(22) PCT Filed: Aug. 24, 2006

(86) PCT No.: PCT/EP2006/065662

§ 371 (c)(1),
(2), (4) Date: Feb. 25, 2008

(87) PCT Pub. No.: WO2007/023182

PCT Pub. Date: Mar. 1, 2007

(65) Prior Publication Data

US 2008/0254116 A1    Oct. 16, 2008

Related U.S. Application Data

(60) Provisional application No. 60/711,738, filed on Aug. 26, 2005, provisional application No. 60/711,737, filed on Aug. 26, 2005, provisional application No. 60/712,206, filed on Aug. 29, 2005.

(51) Int. Cl.
*A61K 31/505* (2006.01)
*A61K 31/501* (2006.01)
*C07D 239/02* (2006.01)

(52) U.S. Cl. .................. 514/252.18; 514/252; 514/272; 544/295; 544/322; 544/331; 544/332

(58) Field of Classification Search ........... 514/252–18, 514/272; 544/295, 331, 332
See application file for complete search history.

(56) References Cited

U.S. PATENT DOCUMENTS 5,521,184 A * 5/1996 Zimmermann ......... 514/252.11

FOREIGN PATENT DOCUMENTS

| WO | 99/03854 | 1/1999 |
|---|---|---|
| WO | 2004/106326 | 12/2004 |
| WO | 2005/077933 | 8/2005 |
| WO | 2005/095379 | 10/2005 |
| WO | 2006/024863 | 3/2006 |
| WO | 2006/048890 | 5/2006 |
| WO | 2006/054314 | 5/2006 |

OTHER PUBLICATIONS

Ansel et al. pp. 89-91, pp. 186-187, Pharmaceutical Dosage forms and Drug delivery systems, 7th edition, Copyright 1999.*

(Continued)

*Primary Examiner*—Ardin Marschel
*Assistant Examiner*—Savitha Rao
(74) *Attorney, Agent, or Firm*—George R. Dohmann

(57) ABSTRACT

The invention relates to the delta and epsilon crystal form of the methanesulfonic acid addition salt of 4-(4-methylpiperazin-1-ylmethyl)-N-[4-methyl-3-(4-(pyridin-3-yl)pyrimidin-2-ylamino)phenyl]-benzamide (the compound of formula I, see below), certain processes for their preparation, pharmaceutical compositions containing these crystal forms, and their use in diagnostic methods or for the therapeutic treatment of warm-blooded animals, and their use as an intermediate or for the preparation of pharmaceutical preparations for use in diagnostic methods or for the therapeutic treatment of warm-blooded animals, especially humans.

27 Claims, 2 Drawing Sheets

(delta form)

OTHER PUBLICATIONS

Morissette et al. Advanced Drug Delivery Reviews 2004, 56, 275-300.*

Hernandez-Boluda et al., "Imatinib Mesylate (GLEEVEC®/GLIVEC®): A New Therapy for Chronic Mueloid Leukemia and Other Malignancies", Drugs of today, 2002, vol. 38 (9), pp. 601-613.

Reichardt P. et al., "Molecular response of gastrointestinal stromal tumor after treatment with tyrosine kinase inhibitor imatinib mesylate", J Clin, Pathol., 2004, vol. 57, pp. 215-217.

Daniels, Craig E. et al., "Imatinib mesylate inhibits the profibrogenic activity of Tgf-β and prevents bleomycin-mediated lung fibrosis", J. Clin. Invest., 2004, vol. 114(9), pp. 1308-1316.

* cited by examiner

FIG. 1 (delta form)
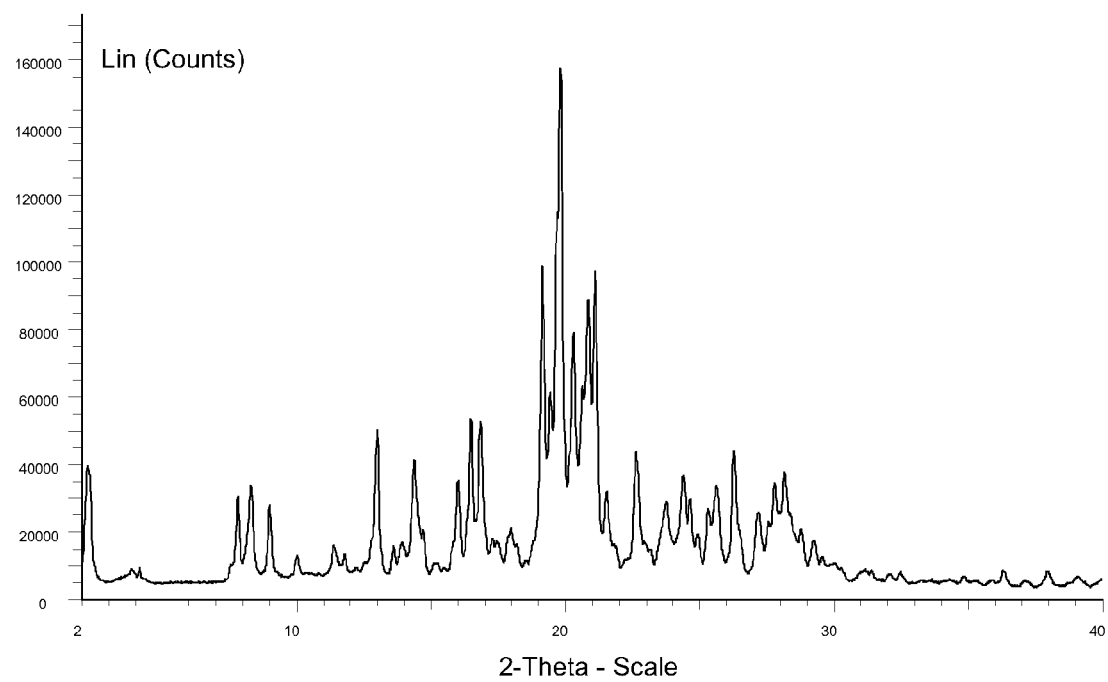

FIG. 2 (epsilon form)
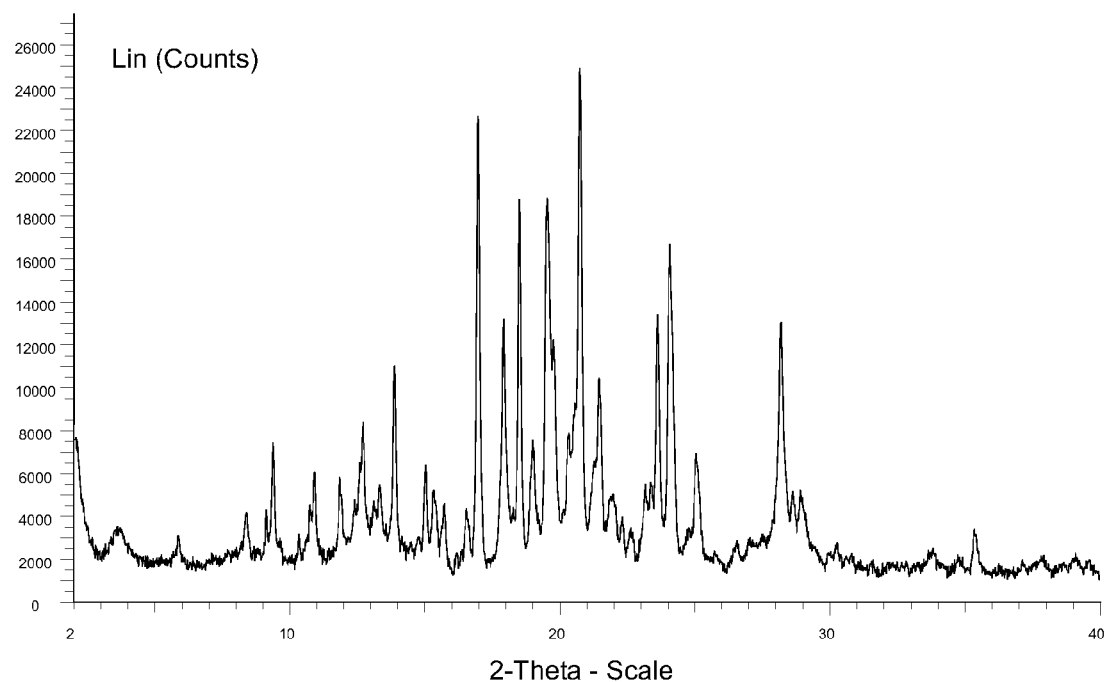

DELTA AND EPSILON CRYSTAL FORMS OF IMATINIB MESYLATE

The invention relates to particular crystal forms of the methanesulfonic acid addition salt of 4-(4-methylpiperazin-1-ylmethyl)-N-[4-methyl-3-(4-(pyridin-3-yl)pyrimidin-2-ylamino)phenyl]-benzamide (the compound of formula I, see below), certain processes for their preparation, pharmaceutical compositions containing these crystal forms, and their use in diagnostic methods or, preferably, for the therapeutic treatment of warm-blooded animals, especially humans, and their use as an intermediate or for the preparation of pharmaceutical preparations for use in diagnostic methods or, preferably, for the therapeutic treatment of warm-blooded animals, especially humans.

BACKGROUND TO THE INVENTION

The preparation of 4-(4-methylpiperazin-1-ylmethyl)-N-[4-methyl-3-(4-(pyridin-3-yl)pyrimidin-2-ylamino)phenyl]-benzamide, also known as Imatinib, and its use, especially as an anti-tumour agent, are described in EP-A-0 564 409, which was published on 6 Oct. 1993, and in equivalent applications in numerous other countries. The compound is exemplified in these publications only in free form (not as a salt).

4-(4-Methylpiperazin-1-ylmethyl)-N-[4-methyl-3-(4-(pyridin-3-yl)pyrimidin-2-ylamino)phenyl]-benzamide mesylate, also known as Imatinib mesylate or STI571, the alpha and the beta crystal form thereof, as well as its pharmaceutical use are described in U.S. Pat. No. 6,894,051. Imatinib mesylate is the active ingredient of the drug Gleevec® (Glivec®) which is an approved medicament for the treatment of Chronic Myeloid Leukemia (CML) and gastrointestinal stromal tumors (GIST). Another polymorph of Imatinib mesylate, the so-called H1-form, is described in WO2004/106326.

It has now been surprisingly found that under conditions new crystal forms of the methanesulfonate salt may be found, which are described hereinafter as δ-crystal form and ε-crystal form, and which have advantageous utilities and properties.

DETAILED DESCRIPTION OF THE INVENTION

The invention is described in more detail in the following with the help of drawings and other aids.

The invention relates especially to essentially pure crystal forms, preferably those which are referred to hereinafter as the δ-crystal and the ε-crystal form form, of the methanesulfonic acid addition salt of Imatinib of formula I,

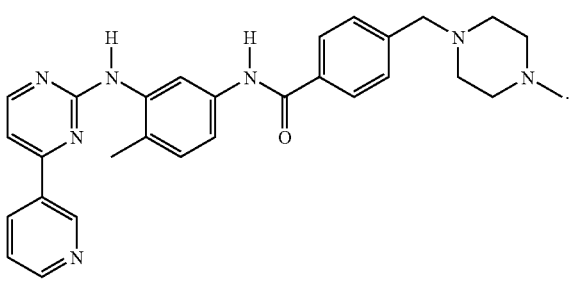

(I)

DESCRIPTION OF THE DRAWINGS

FIG. 1 shows the X-ray diffraction diagram of the δ-crystal form of the methanesulfonic acid addition salt of a compound of formula I. In the X-ray diagram, the angle of refraction 2theta is plotted on the horizontal axis (x-axis) and the relative line intensity (background-corrected peak intensity) on the vertical (y-axis). X-ray powder diffraction patterns are measured on a Bruker D8 with Cu Kα radiation source (Kα1 radiation, wavelength λ=1.54060 Angström). The optical density of the lines on the film is proportional to the light intensity. The film is scanned in using a line scanner. The strongest line in the X-ray diffraction diagram is observed at an angle of refraction 2theta of 19.8° having a relative line intensity of 100%. More broadly, the δ-crystal form is characterized by refractions at angles of refraction 2theta of 19.2° (70), 19.4° (51), 19.8° (100), 20.3° (60), 20.7° (52), 20.9° (65) and 21.1° (69).

In essentially pure material of the δ-crystal form of the methanesulfonic acid addition salt of a compound of formula I, lines can be observed at angles of refraction 2theta 16.5° (44), 16.8° (44), 19.2° (70), 19.4° (51), 19.8° (100), 20.3° (60), 20.7° (52), 20.9° (65), 21.1° (69) and 22.7° (41). Depending on the instruments used for X-ray diffraction analysis and the purity of the analyzed material containing the δ-crystal form of the methanesulfonic acid addition salt of a compound of formula I, it should be possible to observe lines having a relative line intensity of 30% or more at the following angles of refraction 2theta (relative line intensities given in parentheses): 2.2° (35), 13.0° (39), 14.4° (36), 16.0° (34), 16.5° (44), 16.8° (44), 19.2° (70), 19.4° (51), 19.8° (100), 20.3° (60), 20.7° (52), 20.9° (65), 21.1° (69), 21.5° (36), 22.7° (41), 23.7° (33), 24.4° (37), 24.7° (33), 25.3° (31), 25.6° (34), 26.3° (39) and 28.1° (34).

The δ-crystal form of the methanesulfonic acid addition salt of a compound of formula I is also characterized by lines in the X-ray diffraction diagram observed at an angle of refraction 2theta of 7.8, 8.3 and 9.0.

FIG. 2 shows the X-ray diffraction diagram of the ε-crystal form of the methanesulfonic acid addition salt of a compound of formula I. In the X-ray diagram, the angle of refraction 2theta is plotted on the horizontal axis (x-axis) and the relative line intensity (background-corrected peak intensity) on the vertical (y-axis). X-ray powder diffraction patterns are measured on a Bruker D8 with Cu Kα radiation source (Kα1 radiation, wavelength λ=1.54060 Angström). The optical density of the lines on the film is proportional to the light intensity. The film is scanned in using a line scanner. The strongest line in the X-ray diffraction diagram is observed at an angle of refraction 2theta of 20.7° having a relative line intensity of 100%. The ε-crystal form is characterized by refractions at angles of refraction 2theta of (a) 17.0°, said peak having a relative line intensity of 99, (b) 18.5°, said peak having a relative line intensity of 80, (c) 19.6°, said peak having a relative line intensity of 78 and (d) 20.7°, said peak having a relative line intensity of 100. More broadly, the ε-crystal form is characterized by refractions at angles of refraction 2theta of 13.9° (58), 17.0° (99), 17.9° (59), 18.5° (80), 19.6° (78), 20.7° (100) and 24.1° (62).

In essentially pure material of the ε-crystal form of the methanesulfonic acid addition salt of a compound of formula I, lines can be observed at angles of refraction 2theta 12.70 (48), 13.90 (58), 17.0° (99), 17.9° (59), 18.5° (80), 19.6° (78), 20.7° (100), 21.4° (40), 23.6° (49), 24.10 (62) and 28.2° (45). Depending on the instruments used for X-ray diffraction analysis and the purity of the analyzed material containing the ε-crystal form of the methanesulfonic acid addition salt of a compound of formula I, it should be possible to observe lines having a relative line intensity of 30% or more at the following angles of refraction 2theta (relative line intensities given in parentheses): 9.4° (35), 11.9° (36), 12.7° (48), 13.3° (35), 13.9° (58), 15.0° (37), 15.3° (32), 17.0° (99), 17.9° (59), 18.5° (80), 19.0° (34), 19.6° (78), 20.7° (100), 21.4° (40), 23.6° (49), 24.10 (62) and 28.20 (45).

The ε-crystal form of the methanesulfonic acid addition salt of a compound of formula I is also characterized by a line in the X-ray diffraction diagram observed at an angle of refraction 2theta of 9.4.

The term "essentially pure" is understood in the context of the present invention to mean especially that at least 90, preferably at least 95, and most preferably at least 99 percent by weight of the crystals of an acid addition salt of formula I are present in the specified crystal form according to the invention, especially the δ-crystal form or the ε-crystal form.

In the context with stating that the δ-crystal form of the methanesulfonic acid addition salt of a compound of formula I exhibits an X-ray diffraction diagram essentially as in FIG. 1, the term "essentially" means that at least the major lines of the diagram depicted in FIG. 1, i.e. those having a relative line intensity of more than 20%, especially more than 30%, as compared to the most intense line in the diagram, have to be present.

In the context with stating that the ε-crystal form of the methanesulfonic acid addition salt of a compound of formula I exhibits an X-ray diffraction diagram essentially as in FIG. 2, the term "essentially" means that at least the major lines of the diagram depicted in FIG. 2, i.e. those having a relative line intensity of more than 20%, especially more than 30%, as compared to the most intense line in the diagram, have to be present.

The invention expressly relates also to those forms of the methanesulfonic acid addition salt of a compound of formula I in which crystals of the δ-crystal form and/or the ε-crystal form according to the invention are present in essentially pure form along with other crystal forms, in particular the α-crystal form, the β-crystal form, the H1-crystal form and/or the amorphous form of the Imatinib mesylate. Preferred, however, are the δ-crystal form and the ε-crystal form in essentially pure form, respectively.

In one preferred embodiment, the essentially pure methanesulfonic acid addition salt of a compound of formula I in the δ-crystal form shows the X-ray diffraction diagram indicated in FIG. 1.

High preference is also given for the δ-crystal form of the methanesulfonic acid addition salt of a compound of formula I which shows an X-ray diffraction diagram of the type shown in FIG. 1, in which the relative peak intensities of each peak do not deviate by more than 10% from the relative peak intensities in the diagram shown in FIG. 1, especially an X-ray diffraction diagramidentical to that shown in FIG. 1.

In another preferred embodiment, the essentially pure methanesulfonic acid addition salt of a compound of formula I in the ε-crystal form shows the X-ray diffraction diagram indicated in FIG. 2.

High preference is furthermore given for the ε-crystal form of the methanesulfonic acid addition salt of a compound of formula I which shows an X-ray diffraction diagram of the type shown in FIG. 2, in which the relative peak intensities of each peak do not deviate by more than 10% from the relative peak intensities in the diagram shown in FIG. 2, especially an X-ray diffraction diagramidentical to that shown in FIG. 2.

Of particularly high preference are the δ-crystal form and for the ε-crystal form of the methanesulfonic acid addition salt of a compound of formula I obtainable as described in the Examples.

One utility of the δ-crystal form and the ε-crystal form of the methanesulfonic acid addition salt of a compound of formula I is the use as an intermediate for the preparation of a distinct crystal form of the methanesulfonic acid addition salt of a compound of formula I, especially the β-crystal form. The (preferably essentially pure) β-crystal form is obtainable by a) digesting the δ-crystal form of the methanesulfonic acid addition salt of a compound of formula I with a suitable polar solvent, especially an alcohol, most especially methanol, or also a ketone (especially in a mixture with water, for example water/acetone), typically acetone, a N,N-di-lower alkyl-lower alkanecarboxamide, typically N,N-dimethylformamide or -acetamide, or a hydrophilic ether, typically dioxane, preferably in the presence of some water, or mixtures thereof, in suspension at a suitable temperature, preferably a temperature between 20 and 50° C., for example at about 25° C., or b) dissolving the δ-crystal form of the methanesulfonic acid addition salt of a compound of formula I with a suitable polar solvent, such as especially an alcohol, typically methanol or ethanol, a ketone (especially in a mixture with water, for example water/acetone) typically acetone, a N,N-di-lower alkyl-lower alkanecarboxamide, typically N,N-dimethylformamide or -acetamide, or a hydrophilic ether, typically dioxane, or mixtures thereof, preferably in the presence of some water, at a suitable temperature, especially after heating the solvent, or while warming during the dissolution process, in both cases preferably to 25° C. up to the reflux temperature of the reaction mixture, and then initiating crystallisation by adding a small amount of the β-crystal form as seed crystal at a suitable temperature, for example between 0 and 70° C., preferably between 20 and 70° C., or c) digesting the ε-crystal form of the methanesulfonic acid addition salt of a compound of formula I with a suitable polar solvent, especially an alcohol, most especially methanol, or also a ketone (especially in a mixture with water, for example water/acetone), typically acetone, a N,N-di-lower alkyl-lower alkanecarboxamide, typically N,N-dimethylformamide or -acetamide, or a hydrophilic ether, typically dioxane, preferably in the presence of some water, or mixtures thereof, in suspension at a suitable temperature, preferably a temperature between 20 and 50° C., for example at about 25° C., or d) dissolving the ε-crystal form of the methanesulfonic acid addition salt of a compound of formula I with a suitable polar solvent, such as especially an alcohol, typically methanol or ethanol, a ketone (especially in a mixture with water, for example water/acetone) typically acetone, a N,N-di-lower alkyl-lower alkanecarboxamide, typically N,N-dimethylformamide or -acetamide, or a hydrophilic ether, typically dioxane, or mixtures thereof, preferably in the presence of some water, at a suitable temperature, especially after heating the solvent, or while warming during the dissolution process, in both cases preferably to 25° C. up to the reflux temperature of the reaction mixture, and then initiating crystallisation by adding a small amount of the γ-crystal form as seed crystal at a suitable temperature, for example between 0 and 70° C., preferably between 20 and 70° C.

One of the advantages of having access to different crystal forms of the compound of formula I is the fact that distinct crystal forms are prone to incorporate distinct impurities upon crystallization, i.e. an impurity incorporated in crystal form β is not necessarily also incorporated in the crystal form δ or η in the crystal form ε. With other words, preparing consecutively distinct crystal forms of the same material increases the purity of the finally obtained substance. Furthermore, distinct crystal forms display different physical properties such as melting points, hygroscopicities, solubilities, flow properties or thermodynamic stabilities, and, hence, distinct crystal forms allow the choice of the most suitable form for a certain use or aspect, e.g. the use as an intermediate in the process of drug manufacture or in distinct administration forms like tablets, capsules, ointments or solutions.

The δ-crystal form and the ε-crystal form of the methanesulfonic acid addition salt of a compound of formula I possesses valuable pharmacological properties and may, for example, be used as an anti-tumour agent or as an agent to treat restenosis.

The present invention relates especially to the δ-crystal form of the methanesulfonic acid addition salt of a compound of formula I in the treatment of one of the said diseases mentioned herein or in the preparation of a pharmacological agent for the treatment thereof.

Additionally, the present invention relates especially to the ε-crystal form of the methanesulfonic acid addition salt of a compound of formula I in the treatment of one of the said diseases mentioned herein or in the preparation of a pharmacological agent for the treatment thereof.

The antiproliferative, especially anti-tumour, activity of the methanesulfonic acid addition salt of a compound of formula I in vivo is, for example, described for the treatment of abl-dependent tumours in Nature Med. 2, 561-6 (1996).

The invention relates also to a method for the treatment of warm-blooded animals suffering from said diseases, especially leukemia, wherein a quantity of the δ-crystal form or of the crystal form of the methanesulfonic acid addition salt of a compound of formula I which is effective against the disease concerned, especially a quantity with antiproliferative efficacy, is administered to warm-blooded animals in need of such treatment. The invention relates moreover to the use of the δ-crystal form or of the ε-crystal form of the methanesulfonic acid addition salt of a compound of formula I for the preparation of pharmaceutical compositions for use in treating the human or animal body, especially for the treatment of tumours, such as gliomas or prostate tumours.

In preferred embodiments, the present invention relates to the use in of the δ-crystal form or of the ε-crystal form of the methanesulfonic acid addition salt of a compound of formula I in the treatment of one of the disorders listed below:

1. metastatic, inoperable GIST,
2. advanced chronic myeloid leukemia,
3. newly diagnosed chronic myeloid leukemia,
4. pediatric Philadelphia chromosome-positive chronic myeloid leukemia,
5. Philadelphia chromosome-positive acute lymphocytic leukemia (ALL),
6. glioblastoma multiforme, preferably in combination with hydroxyurea,
7. dermatofibrosarcoma protuberans (DFSP),
8. hypereosinophilic sindrome (HES), and
9. chronic myelomonocytic leucemia (CMML).

Depending on species, age, individual condition, mode of administration, and the clinical picture in question, effective doses, for example daily doses of about 50-2500 mg, preferably 100-1000 mg, especially 250-800 mg, of Imatinib mesylate having the δ-crystal form or the ε-crystal form are administered to warm-blooded animals of about 70 kg bodyweight. Preferably, daily dosages of 400 mg or 600 mg are administered orally once daily, preferably together with a meal and a large glass of water (about 200 mL).

800 mg daily dosages are preferably administered in the form of 400 mg dosages twice daily together with food.

The δ-crystal form and the ε-crystal form described herein can be utilized to prepare stable pharmaceutical dosage forms. Hence, the invention relates also to pharmaceutical preparations which contain an amount, especially an effective amount for prevention or treatment of one of the diseases mentioned herein, of the methanesulfonic acid addition salt of a compound of formula I in the δ-crystal form or the ε-crystal form, together with pharmaceutically acceptable carriers which are suitable for topical, enteral, for example oral or rectal, or parenteral administration and may be inorganic or organic and solid or liquid. Especially tablets or gelatin capsules containing the active substance together with diluents, for example lactose, dextrose, sucrose, mannitol, sorbitol, cellulose, and/or glycerin, and/or lubricants, for example silica, talc, stearic acid, or salts thereof, typically magnesium or calcium stearate, and/or polyethylene glycol, are used for oral administration. Tablets may likewise contain binders, for example magnesium aluminium silicate, starches, typically corn, wheat or rice starch, gelatin, methylcellulose, sodium carboxymethylcellulose and/or polyvinylpyrrolidone, and, if so desired, disintegrants, for example starches, agar, alginic acid, or a salt thereof, typically sodium alginate, and/or effervescent mixtures, or adsorbents, colouring agents, flavours, and sweetening agents. The pharmacologically active compounds of the present invention may further be used in the form of preparations for parenteral administration or infusion solutions. Such solutions are preferably isotonic aqueous solutions or suspensions, these possibly being prepared before use, for example in the case of lyophilised preparations containing the active substance either alone or together with a carrier, for example mannitol. The pharmaceutical substances may be sterilised and/or may contain excipients, for example preservatives, stabilisers, wetting agents and/or emulsifiers, solubilisers, salts for the regulation of osmotic pressure, and/or buffers. The present pharmaceutical preparations which, if so desired, may contain further pharmacologically active substances, are prepared in a manner known per se, for example by means of conventional mixing, granulating, coating, dissolving or lyophilising processes, and contain from about 1% to 100%, especially from about 1% to about 20%, of the active substance or substances. In a preferred embodiment, the tablet or capsule contains 50 mg 100 mg of the of the methanesulfonic acid addition salt of a compound of formula I in the δ-crystal form, optionally together with pharmaceutically acceptable carriers.

In one embodiment, the capsule is a hard gelatine capsule containing a dry powder blend. The capsule shell preferably contains gelatine and titanium dioxide as well as red iron oxide. The ratio of weight of capsule fill to capsule shell is preferably between about 100:25 and 100:50, more preferably between 100:30 and 100:40.

In another embodiment, a film coated tablet is used comprising 100 mg, 400 mg or 800 mg drug substance together with inactive excepients selected from colloidal anhydrous silica, polyvinylpyrrolidone, magnesium stearate and microcrystalline cellulose.

The following Examples illustrate the invention without limiting the scope thereof. Temperatures are given in degrees Celsius (° C.).

EXAMPLES

Example 1

Preparation of Crystalline Form Delta of Imatinib Mesylate Using Acetone and Methanol About 500 mg of Imatinib mesylate is first dissolved in about 100 ml of water. A micro reactor is charged with about 50 μl of this aqueous solution of Imatinib mesylate. The solution is flushed with nitrogen at room temperature to dry the solution. The dry precipitate is re-suspended with about 125 μl amounts of each, acetone and methanol. The suspension is aged at about 45-55° C. for about 2 hrs. The solution is then allowed to evaporate at 45° C. to 55° C. under a stream of nitrogen.

Example 2

Tablets with Imatinib Mesylate, δ-Crystal Form

Tablets containing 100 mg of the active substance named in the title are usually prepared in the following composition:

| Composition | |
|---|---|
| Active ingredient | 100 mg |
| Crystalline lactose | 240 mg |
| Avicel | 80 mg |
| PVPPXL | 20 mg |
| Aerosil | 2 mg |
| Magnesium stearate | 5 mg |
| | 447 mg |

Preparation: The active substance is mixed with carrier materials and compressed on a tableting machine (Korsch EKO, punch diameter 10 mm).
Avicel is microcrystalline cellulose (FMC, Philadelphia, USA).
PVPPXL is polyvinylpolypyrrolidone, cross-linked (BASF, Germany).
Aerosil is silicon dioxide (Degussa, Germany).

Example 3

Capsules with Imatinib Mesylate, δ-Crystal Form

Capsules containing 100 mg of the compound named in the title as active substance are usually prepared in the following composition:

| Composition | |
|---|---|
| Active ingredient | 100 mg |
| Avicel | 200 mg |
| PVPPXL | 15 mg |
| Aerosil | 2 mg |
| Magnesium stearate | 1.5 mg |
| | 318.5 mg |

The capsules are prepared by mixing the components and filling the mixture into hard gelatin capsules, size 1.

Example 4

Preparation of Crystalline Form Epsilon of Imatinib Mesylate Using Ethyl Acetate and Ethanol About 500 mg of Imatinib mesylate drug substance is first dissolved in about 100 ml of water. A micro reactor is charged with about 50 μl of this aqueous solution of Imatinib mesylate. The solution is flushed with nitrogen at room temperature to dry the solution. The dry precipitate is resuspended with about 125 μl amounts of each, ethyl acetate and 95% ethanol. The suspension is aged at about 45-55° C. for about 2 hrs. The solution is then allowed to evaporate at 45° C. to 55° C. under a stream of nitrogen.

Example 5

Tablets with Imatinib Mesylate, ε-Crystal Form

Tablets containing 100 mg of the active substance named in the title are usually prepared in the following composition:

| Composition | |
|---|---|
| Active ingredient | 100 mg |
| Crystalline lactose | 240 mg |
| Avicel | 80 mg |
| PVPPXL | 20 mg |
| Aerosil | 2 mg |
| Magnesium stearate | 5 mg |
| | 447 mg |

Preparation: The active substance is mixed with carrier materials and compressed on a tableting machine (Korsch EKO, punch diameter 10 mm).
Avicel is microcrystalline cellulose (FMC, Philadelphia, USA).
PVPPXL is polyvinylpolypyrrolidone, cross-linked (BASF, Germany).
Aerosil is silicon dioxide (Degussa, Germany).

Example 6

Capsules with Imatinib Mesylate, ε-Crystal Form

Capsules containing 100 mg of the compound named in the title as active substance are usually prepared in the following composition:

| Composition | |
|---|---|
| Active ingredient | 100 mg |
| Avicel | 200 mg |
| PVPPXL | 15 mg |
| Aerosil | 2 mg |
| Magnesium stearate | 1.5 mg |
| | 318.5 mg |

The capsules are prepared by mixing the components and filling the mixture into hard gelatin capsules, size 1.

What is claimed is:
1. A delta crystalline form of the methanesulfonic acid addition salt of a compound of formula I

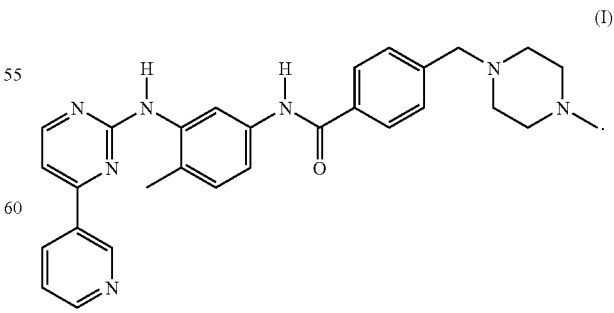

which shows X-ray diffraction peaks at an angle of refraction 2theta of (a) 7.8°, (b) 8.3° and (c) 9.0°.

2. The crystalline form according to claim 1, which shows on X-ray diffraction additional peaks at an angle of refraction 2theta of 19.2° and 19.8°.

3. The crystalline form according to claim 1, which shows on X-ray diffraction additional peaks at an angle of refraction 2theta of 19.2°, 19.8°, said peak at 19.8° having a relative line intensity of 100, and 21.1°.

4. The crystalline form according to claim 1, which shows in an X-ray diffraction diagram additional lines at the following angles of refraction 2theta: 19.2, 19.4°, 19.8, 20.3°, 20.7°, 20.9° and 21.1°.

5. The crystalline form according to claim 1, which shows in an X-ray diffraction diagram additional lines at the following angles of refraction 2theta: 16.5°, 16.8°, 19.2°, 19.4°, 19.8°, 20.3°, 20.7°, 20.9°, 21.1° and 22.7°.

6. The crystalline form of the methanesulfonic acid addition salt of a compound of formula I according to claim 1, which is present in essentially pure form.

7. A crystalline form of the methanesulfonic acid addition salt of a compound of formula I

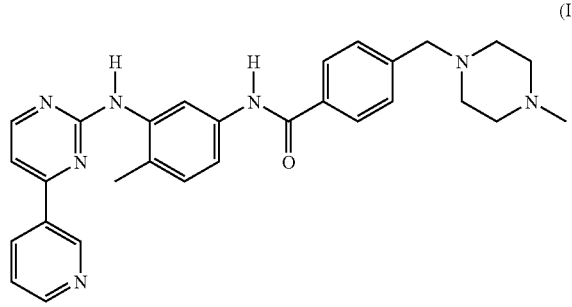

(I)

which shows in an X-ray diffraction diagram lines at the following angles of refraction 2theta (relative line intensities given in parentheses): 16.5° (44), 16.8° (44), 19.2° (70), 19.4° (51), 19.8° (100), 20.3° (60), 20.7°-(52), 20.9° (65), 21.1° (69) and 22.7° (41), in which the relative peak intensities of each peak do not deviate by more than 10%.

8. An epsilon crystalline form of the methanesulfonic acid addition salt of a compound of formula I

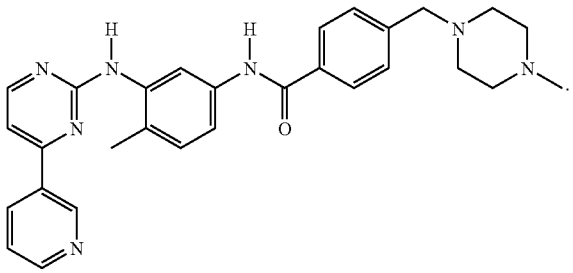

(I)

which shows on X-ray diffraction peaks at an angle of refraction 2theta of (a) 9.4° and (b) 28.2°.

9. The crystalline form according to claim 8, which shows on X-ray diffraction additional peaks at an angle of refraction 2theta of 17.0°, 18.5 °, 19.6° and 20.7°.

10. The crystalline form according to claim 8 which shows on X-ray diffraction additional peaks at an angle of refraction 2theta of 17.0°, 18.5°, and 20.7°, said peak at 20.7° having a relative line intensity of 100.

11. The crystalline form according to claim 8, which shows in an X-ray diffraction diagram additional lines at the following angles of refraction 2theta: 13.9°, 17.0°, 17.9°, 18.5°, 19.6°, 20.7° and 24.1°.

12. The crystalline form according to claim 8, which shows in an X-ray diffraction diagram additional lines at the following angles of refraction 2theta: 12.7 °, 13.9°, 17.0°, 17.9°, 18.5°, 19.6°, 20.7°, 21.4°, 23.6°, 24.1° and 28.2°.

13. The crystalline form according to claim 8, which is present in essentially pure form.

14. A crystalline form of the methanesulfonic acid addition salt of a compound of formula I

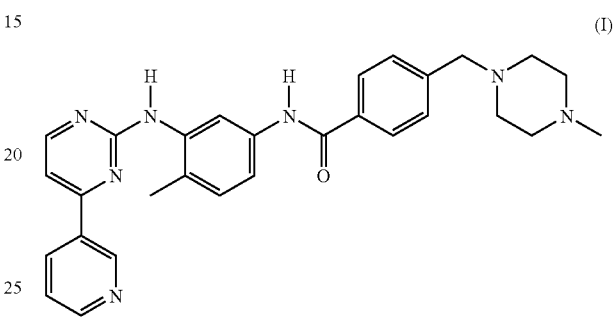

(I)

which shows in an X-ray diffraction diagram lines at the following angles of refraction 2theta (relative line intensities given in parentheses): 12.7° (48), 13.9° (58), 17.0° (99), 17.9° (59), 18.5° (80), 19.6° (78), 20.7° (100), 21.4° (40), 23.6° (49), 24.1° (62) and 28.2° (45), in which the relative peak intensities of each peak do not deviate by more than 10%.

15. A composition containing the methanesulfonic acid addition salt of a compound of formula I

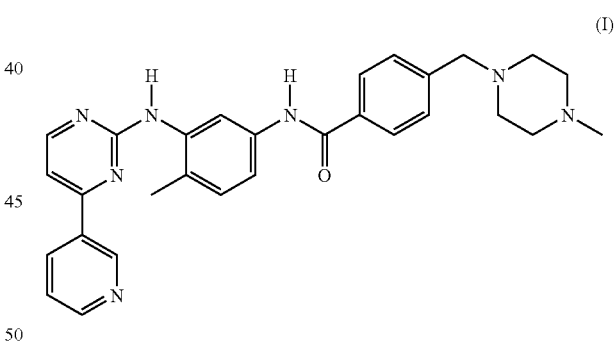

(I)

comprising a crystalline form of the methanesulfonic acid addition salt of a compound of formula I according to claim 1.

16. The composition according to claim 15 comprising additionally at least one distinct form of the methanesulfonic acid addition salt of a compound of formula I selected from the amorphous form, the α-crystal form, the β-crystal form and the H1-crystal form.

17. A pharmaceutical composition comprising a crystalline form of the methanesulfonic acid addition salt of a compound of formula I according to claim 1, and optionally at least one pharmaceutically acceptable carrier.

18. The pharmaceutical composition according to claim 17 comprising additionally at least one distinct form of the methanesulfonic acid addition salt of a compound of formula I selected from the amorphous form, the α-crystal form, the β-crystal form and the H1-crystal form.

19. The pharmaceutical composition according to claim 17 comprising between 50 mg and 800 mg of a crystalline form of the methanesulfonic acid addition salt of a compound of formula I.

20. The pharmaceutical composition according claim 17 which is a capsule containing a dry powder blend comprising between 50 mg and 200 mg of a crystalline form of the methanesulfonic acid addition salt of a compound of formula I.

21. The capsule according to claim 20, wherein the shell contains gelatine.

22. The capsule according to claim 20, wherein the shell contains titanium dioxide.

23. The capsule according to claim 20, wherein the shell contains red iron oxide.

24. The capsule according to claim 20, wherein the ratio of weight of capsule fill to capsule shell is between about 100:25 and 100:50.

25. The capsule according to claim 20, wherein the ratio of weight of capsule fill to capsule shell is between 100:30 and 100:40.

26. The pharmaceutical composition according to claim 17 which is a tablet comprising 100 mg, 400 mg or 800 mg drug substance together with inactive excepients.

27. The tablet according to claim 26 wherein the inactive excepients are selected from colloidal anhydrous silica, polyvinylpyrrolidone, magnesium stearate and microcrystalline cellulose.

* * * * *